United States Patent
Mallmann et al.

(10) Patent No.: US 7,847,165 B2
(45) Date of Patent: *Dec. 7, 2010

(54) TOBACCO CULTIVAR AOB 175

(75) Inventors: Irno L. Mallmann, Santa Cruz do Sul (BR); Claudir Lorencetti, Vera Cruz (BR)

(73) Assignee: Alliance One International, Inc., Morrisville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/688,354

(22) Filed: Jan. 15, 2010

(65) Prior Publication Data

US 2010/0132064 A1      May 27, 2010

Related U.S. Application Data

(63) Continuation of application No. 11/935,977, filed on Nov. 6, 2007, now Pat. No. 7,667,106.

(51) Int. Cl.
  *C12N 15/04*  (2006.01)
  *C12N 15/82*  (2006.01)
  *A01H 5/00*   (2006.01)
  *A01H 5/10*   (2006.01)
  *A01H 1/00*   (2006.01)

(52) U.S. Cl. .................. 800/317.3; 800/260; 800/265; 800/278; 800/279; 800/300; 800/301; 800/302; 800/303; 435/414

(58) Field of Classification Search .................. None
See application file for complete search history.

(56) References Cited

U.S. PATENT DOCUMENTS 7,667,106 B2 * 2/2010 Mallmann et al. ......... 800/317.3
2006/0191039 A1   8/2006 Conkling et al.
2006/0237025 A1  10/2006 Conkling et al.
2007/0199097 A1   8/2007 Xu et al.

FOREIGN PATENT DOCUMENTS

FR       2 597 299 A    10/1987

OTHER PUBLICATIONS

Legg et al. "Breeding and Genetics," In: *Tobacco: Production, Chemistry and Technology* Edited by D. Layten Davis and Mark T. Nielsen, p. 36 (1999).
Luciani et al. "The Protection of Tobacco Varieties with the UPOV System in the EU," (Agronomy and Phytopathology) 2006 Coresta Congress, Paris, France, Slide Show Presentation (8 pages) (Oct. 15-20, 2006).
Luciani et al. "The Protection of Tobacco Varieties with the UPOV System in the EU," (Agronomy and Phytopathology) 2006 Coresta Meeting, Paris, France, (10 pages) (Oct. 15-20, 2006).
Berbeć and Laskowska. "Agronomic Performance of Flue-Cured Tobacco $F_1$ Hybrids Obtained With Different Sources of Male Sterile Cytoplasm" *Contributions to Tobacco Research* 21(4):234-239 (2004).
Hernould et al. "Male-Sterility Induction in Transgenic Tobacco Plants With an Unedited *atp9* Mitochondrial Gene From Wheat" *Proc. Natl. Acad. Sci. USA* 90:2370-2374 (1993).
International Search Report and Written Opinion of International Application No. PCT/US2008/012504, mailed Apr. 2, 2009 (17 pages).
Kidd et al. "The *A* and *B* Loci in Tobacco Regulate a Network of Stress Response Genes, Few of Which are Associated With Nicotine Biosynthesis" *Plant Molecular Biology* 60:699-716 (2006).

* cited by examiner

*Primary Examiner*—Russell Kallis
(74) *Attorney, Agent, or Firm*—Myers Bigel Sibley & Sajovec, P.A.

(57) ABSTRACT

The present invention relates to a novel tobacco cultivar designated AOB 175, which has low to intermediate nicotine content. The invention provides seeds of the cultivar AOB 175, plants and parts thereof of the cultivar AOB 175, a tissue culture derived from the cultivar AOB 175, hybrids produced from cultivar AOB 175 and lines derived from cultivar AOB 175, as well as genetically modified forms of the foregoing plants and tissue culture. Also provided are methods of producing cultivar AOB 175 plants, cultivar AOB 175 hybrid plants, and tobacco lines derived from cultivar AOB 175. In addition, products produced from the plants of the present invention are provided.

5 Claims, No Drawings

TOBACCO CULTIVAR AOB 175

RELATED APPLICATIONS

This application is a continuation application of, and claims priority to, U.S. application Ser. No. 11/935,977, having a filing date of Nov. 6, 2007, now issued as U.S. Pat. No. 7,667,106 on Feb. 23, 2010, the entire contents of which is incorporated by reference herein.

FIELD OF THE INVENTION

The present invention relates to tobacco breeding, in particular, to a new tobacco cultivar designated AOB 175 having low to intermediate nicotine content.

BACKGROUND OF THE INVENTION

Tobacco (*Nicotiana tabacum* L.) is an important commercial crop in the United States as well as in other countries. The production of tobacco with decreased levels of nicotine is of interest. Various processes have been designed for the removal of nicotine from tobacco. However, most of these processes remove other ingredients from tobacco in addition to nicotine, thereby adversely affecting the tobacco.

There are numerous stages in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The aim is to combine in a single variety an improved combination of desirable traits from the parental germplasm. These important traits may include higher yield, resistance to diseases and insects, better stems and roots, tolerance to drought and heat, improved nutritional quality, and better agronomic characteristics.

Choice of breeding methods depends on the mode of plant reproduction, the heritability of the trait(s) being improved, and the type of cultivar used commercially (e.g., $F_1$ hybrid cultivar, pure line cultivar, etc.). For highly heritable traits, a choice of superior individual plants evaluated at a single location may be effective, whereas for traits with low heritability, selection can be based on mean values obtained from replicated evaluations of families of related plants. Popular selection methods commonly include pedigree selection, modified pedigree selection, mass selection, and recurrent selection.

The complexity of inheritance influences the choice of breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program generally includes a periodic, objective evaluation of the efficiency of the breeding procedure. Evaluation criteria vary depending on the goals and objectives, but should include gain from selection per year based on comparisons to an appropriate standard, overall value of the advanced breeding lines, and number of successful cultivars produced per unit of input (e.g., per year, per dollar expended, etc.).

The development of new tobacco hybrids involves the development and selection of tobacco breeding lines, the crossing of these breeding lines and selection of superior hybrid crosses. Hybrid combinations are identified and developed on the basis of certain single gene traits such as leaf size or color, flower color, disease resistance or herbicide resistance, and the like, which are expressed in a hybrid. Additional data, such as yield and quality traits, on parental lines as well as the phenotype of the hybrid influence the breeder's decision to continue with the specific hybrid cross.

Pedigree breeding and recurrent selection breeding methods are used to develop true breeding cultivars from breeding populations. Breeding programs combine desirable traits from two or more cultivars or various broad-based sources into breeding pools from which cultivars are developed by selfing or alternatively, by creating doubled-haploids, and selection of desired phenotypes. The new cultivars are evaluated to determine which have commercial potential.

Pedigree breeding is commonly used for the improvement of self-pollinating crops and parental lines for hybrids. Two parents which possess favorable, complementary traits are crossed to produce an $F_1$. An $F_2$ population is produced by selfing one or several $F_1$ plants. Selection of the best individuals may begin in the $F_2$ population; then, beginning in the $F_3$, the best individuals in the families are selected. Replicated testing of families can begin in the $F_4$ generation to improve the effectiveness of selection for traits with low heritability. At an advanced stage of inbreeding (i.e., $F_6$ and $F_7$), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$, individuals. The number of plants in a population may decline in each generation due to failure of some seeds to germinate or some plants to produce at least one seed. As a result, not all of the $F_2$ plants originally sampled in the population will be represented by a progeny when generation advance is completed.

In a multiple-seed procedure, tobacco breeders harvest seeds from one or more flowers from each plant in a population and pool them to form a bulk. Part of the bulk is used to plant the next generation and part is put in reserve. The procedure has been referred to as modified single-seed descent technique.

Proper testing should detect any major faults and establish the level of superiority or improvement over current cultivars.

In addition to showing superior performance, the breeder should consider whether there is a demand for a new cultivar that is compatible with industry standards or which creates a new market. The introduction of a new cultivar will incur additional costs to the seed producer, the grower, the processor and the consumer, for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Methods of tobacco breeding are discussed in detail in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, NY. 761 pp.

SUMMARY OF THE INVENTION

The present invention relates to a new and distinctive tobacco cultivar designated AOB 175 having desirable agronomic and smoking characteristics in combination with low to intermediate nicotine content.

The invention further provides seeds of the cultivar AOB 175, plants of the cultivar AOB 175 and parts thereof, for example, leaves, pollen, embryos, cotyledons, hypocotyls, roots, root tips, anthers, flowers, ovules, shoots, stems, stalks, pith and capsules, tissue culture comprising tissue, callus, cells or protoplasts of the cultivar AOB 175, hybrids having a cultivar AOB 175 parent or ancestor, and AOB 175 derived tobacco plants, as well as genetically modified (e.g., by conventional breeding or genetic engineering techniques) forms of the foregoing plants and tissue culture.

The present invention further provides methods of producing a tobacco plant by crossing the AOB 175 cultivar with itself or a different tobacco line. The invention further relates to methods for producing other tobacco cultivars or breeding lines derived from the cultivar AOB 175 by crossing the AOB 175 cultivar with a second tobacco plant and growing the progeny seed to yield an AOB 175-derived tobacco plant. An additional embodiment of the invention provides a method for a tobacco plant that contains in its genetic material one or more transgenes, comprising crossing an AOB 175 cultivar containing one or more transgenes with either a second plant of another tobacco line, or a non-transformed AOB 175 tobacco plant, wherein progeny are produced, so that the genetic material of the progeny that result from the cross comprise the transgene(s) optionally operably linked to one or more regulatory elements.

Another aspect of the invention provides a method for developing a tobacco plant in a tobacco plant breeding program using plant breeding techniques, which includes employing an AOB 175 tobacco plant or a part thereof, or an AOB 175-derived tobacco plant, or a part thereof, as a source of plant breeding material, wherein the plant breeding techniques are selected from the group consisting of recurrent selection, backcrossing, pedigree breeding, restriction fragment length polymorphism enhanced selection, genetic marker enhanced selection, double haploid breeding, single seed descent, multiple seed descent, and transformation.

A further aspect of the present invention provides products comprising tobacco wherein the tobacco further comprises tobacco from the plants of the present invention, and parts thereof.

These and other aspects of the invention are set forth in more detail in the description of the invention below.

DETAILED DESCRIPTION OF THE INVENTION

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

As used in the description of the invention and the appended claims, the singular forms "a", "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of a compound (e.g., an amount of nicotine) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP §2111.03. Thus, the term "consisting essentially of" when used in a claim of this invention is not intended to be interpreted to be equivalent to "comprising."

As used herein, the term "plant" includes plant cells, plant protoplasts and plant tissue (e.g., in culture; tissue culture) from which tobacco plants can be regenerated, plant calli, plant clumps, and plant cells that are intact in plants or parts of plants, such as leaves, pollen, embryos, cotyledon, hypocotyl, roots, root tips, anthers, flowers and a part thereof, ovules, shoots, stems, stalks, pith, capsules, and the like.

As used herein, the term "tissue culture" encompasses cultures of tobacco tissue, cells, protoplasts and callus. Methods of culturing tobacco tissue, cells, protoplasts and callus, as well as methods of regenerating plants from tobacco tissue cultures are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, NY. 761 pp.

As used herein, the term "resistance" and the term "tolerance" refer to the ability of a plant to withstand exposure to an insect, a disease or pathogen, an herbicide or other agent or condition (abiotic or biotic). A resistant or tolerant plant variety will have a level of resistance or tolerance, respectively, that is higher than a comparable wild-type variety.

Description of the Variety

A breeder uses various methods to help determine which plants should be selected from segregating populations and ultimately which inbred lines will be used to develop hybrids for commercialization. In addition to knowledge of the germplasm and plant genetics, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest.

In the case of the present tobacco variety, AOB 175, selection for each generation was initially made based on field observations of various phenotypic characteristics such as degree of maturity, number of leaves per plant, leaf insertion angle, leaf size (width and length), internode distance, and lamina-midrib ratio. The leaves of the selected plants were harvested, cured and then analyzed for nicotine content. The plants finally selected for each generation were those having reduced nicotine content as described below.

AOB 175 was the result of an initial cross between the tobacco varieties LI BY 21 and TN 90, which was carried out in Vera Cruz/Rio Grande do Sul (Latitude: 29°42'53"S; Longitude: 52°30'20"W), Brazil during the crop season of 1997/1998. The $F_1$ seeds were sown in the greenhouse during the winter season of 1998 and the $F_2$ seeds were produced through self-pollination of the $F_1$ plants.

In the 1999/2000 crop season, the $F_2$ seeds were sown and 90 plants were transplanted into the field in Vera Cruz/Rio Grande do Sul, Brazil. Of these 90 plants, 50 were selected based on field observations as described above. The leaves from these 50 plants were harvested, cured and then analyzed for their nicotine content. Those plants with nicotine levels falling between the population average and the population average minus one standard deviation were selected to give rise to the $F_3$ generation. Accordingly, based on the results of the nicotine analysis, six $F_2$ plants were selected to give rise to six separate $F_3$ families (designated as 00/LABS-25; 00/LABS-27; 00/LABS-28; 00/LABS-32; 00/LABS-33; and 00/LABS-34). For the variety AOB 175, the 00/LABS-32 family formed the $F_3$ generation.

In the 2000/2001 crop season, the 00/LABS-32 $F_3$ seeds were sown and 70 plants were transplanted into a field in Vera Cruz/Rio Grande do Sul, Brazil. Fifty plants were selected from the 70 $F_3$ plants based on phenotypic characteristics, as described above, and their leaves were analyzed for nicotine content. Those plants with nicotine levels falling between the population average and the population average minus one standard deviation were selected to give rise to the $F_4$ generation. Accordingly, based on the results of the nicotine analysis, five of the fifty $F_3$ plants were selected and their seeds were bulked and used to form two separate $F_4$ populations (designated 01/LABS-19 and 01/LABS-20).

In the 2001/2002 crop season, the 01/LABS-20 $F_4$ seeds were sown and 50 $F_4$ plants were transplanted into a field in Vera Cruz/Rio Grande do Sul, Brazil. Twenty-five plants were then selected based on phenotypic characteristics, as described above, and their leaves were analyzed for nicotine content. Those plants with nicotine levels falling between the population average plus one standard deviation and the population average minus one standard deviation were selected to give rise to the $F_5$ generation. Thus, based on the nicotine analysis results, nine out of the twenty-five $F_4$ plants were selected and their seeds bulked, giving rise to the $F_5$ generation (02/LABS-17).

During the 2002/2003 crop season, the 02/LABS-17 seeds were sown and 60 $F_5$ plants were transplanted into the field at Palmitos/Santa Catarina, Brazil (Latitude: 27°04'03"S; Longitude: 53°09'40"W). Of the 60 $F_5$ plants, 20 were selected based on phenotypic characteristics observed in the field, as described above and their leaves analyzed for nicotine content. Those plants with nicotine levels falling between the population average plus one-half the standard deviation and the population average minus one-half the standard deviation were selected to give rise to the $F_6$ generation. Accordingly, based on the results of the nicotine analysis, thirteen of the $F_5$ plants were selected and their seeds bulked, giving rise to the $F_6$ generation (designated 03/LABS-175).

In the 2003/2004 crop season, the 03/LABS-175 $F_6$ seeds were sown and 60 plants were transplanted into the field at Palmitos/Santa Catarina, Brazil. Out of the 60 plants, 20 were selected as described previously and analyzed for their nicotine content. Those plants with nicotine levels falling between the population average plus one-half the standard deviation and the population average minus one-half the standard deviation were selected to give rise to the $F_7$ generation. Accordingly, seven plants out of the twenty $F_6$ plants were selected and their seeds bulked, giving rise to the $F_7$ generation (designated LABS 175 or AOB 175).

During the 2004/2005 crop season, the AOB 175 $F_7$ seeds were sown and 144 $F_7$ plants were transplanted into the field at Palmitos/Santa Catarina, Brazil. Of the 144 plants, twenty were selected based on phenotypic characteristics, as described previously, and their leaves analyzed for nicotine content. Similar to the previous two generations, those plants with nicotine levels falling between the population average plus one-half the standard deviation and the population average minus one-half the standard deviation were selected to give rise to the next generation ($F_8$). Thus, based on the results of the nicotine analysis, seven $F_7$ plants were selected and their seeds were bulked, giving rise to the $F_8$ generation and to the foundation seed of AOB 175.

The variety AOB 175, having been observed for eight generations, is considered uniform and stable. The variety AOB 175 shows no variant plants other than what would normally be expected due to environmental conditions.

Table 1 provides morphological data and other characteristics of the variety AOB 175.

TABLE 1

AOB 175 Variety Description Information.

| | |
|---|---|
| Class | 3 (Burley) |
| Maturity Class | 3 (late) |
| Days to Maturity | 83 |
| Height Class | 3 (tall) |
| Plant Height (cm) | |
| Topped Normal | 163 |
| Not Topped (height to crowfoot) | 206 |
| Leaf Length (cm) | |
| 5th leaf | 64 |
| 10th leaf | 66 |
| 15th leaf | 63.4 |
| Leaf Length Class ($10^{th}$ leaf or center of plant) | 2 (medium) |
| Leaf Width (cm) | |
| 5th leaf | 31 |
| 10th leaf | 30.6 |
| 15th leaf | 28 |
| Leaf Width Class ($10^{th}$ leaf or center of plant) | 3 (medium) |
| Leaf Angle (degrees) | |
| 5th leaf | 77 |
| 10th leaf | 72 |
| 15th leaf | 62 |
| Leaf Angle Class ($10^{th}$ leaf or center of plant) | 4 (drooping) |
| Leaf Yield (Kg/ha) | 2,950 |

TABLE 1-continued

AOB 175 Variety Description Information.

| Leaf Number per plant (not including 2 bed leaves) | |
|---|---|
| Topped Normal | 21.6 |
| Not Topped (number of leaves or nodes to crowfoot from first harvestable leaf) | 25.8 |
| Internode Length Class | 1 (short) |
| Internode Length (mm) | 46 |
| Stalk Diameter Class | 1 (small) |
| Leaf Carriage | Not Arched |
| Tip Shape | Acuminate |
| Leaf Margin | Wavy |
| Leaf Color | Green |
| Venation Pattern | Square |
| Leaf Margin Curving | Not Recurved |
| Leaf Shape | Broadcast at middle of leaf |
| Leaf Surface | Puckered |

| Flowers | |
|---|---|
| Color | Pink |
| Head Habit | Intermediate |
| Plant Form | Pyramidal |
| Ground Suckers (per plant) | 0.2 |

| Disease | |
|---|---|
| Bacterial Wilt | Susceptible |
| Potato Virus Y | Susceptible |
| Tobacco Vein Mottling Virus | Susceptible |
| Tobacco Mosaic Virus | High Resistance |
| Tobacco Etch Virus | Susceptible |

| Leaf Constituents | |
|---|---|
| % Nicotine | 3.66 |
| % Nor Nicotine | 0.08 |
| % Total Nitrogen | 3.49 |

The classes for specific characteristics that are set forth in Table 1 are those defined by the United States Plant Variety Protection Office (See, Exhibit C for tobacco).

Further characteristics of AOB 175 are provided in Tables 2-4, which compare yield, grade index and nicotine content of the new variety with each of its parents, the tobacco varieties LI BY 21 and TN 90 over several different growing seasons. In each case the asterix (*) indicates no significant differences were observed between the averages with the same letter in the same column (by DUNCAN test at 5% probability).

Table 2 presents data from the 2004/05 crop season in which experiments were conducted at two locations: Pinhalzinho/Santa Catarina (Latitude: 26°50'53"S; Longitude: 52°59'31"W) and Vila Maria/Rio Grande do Sul (Latitude: 28°32'05"S; Longitude: 52°09'13"W). The experiments were conducted following a randomized design with three repetitions and 48 plants to each plot. The plants were spaced 45 cm apart with 115 cm between lines (19,523 plants/ha). The total nitrogen used was 234 and 247 kg/ha, respectively. Harvesting occurred at 45 and 42 days after topping, respectively.

TABLE 2

Mean yield, grade index and nicotine of check cultivars an AOB 175 grown at the Pinhalzinho/SC and Vila Maria/RS, Brazil, during the 2004/05 crop season.

| Variety | Yield (Kg/ha) | Grade Index | Nicotine (%) |
|---|---|---|---|
| Pinhalzinho/Santa Catarina | | | |
| TN 90 | 3,311 a* | 59.5 a | 5.26 a |
| LI BY 21 | 2,949 a | 49.3 a | 2.60 b |
| AOB 175 | 3,183 a | 48.0 a | 2.64 b |

TABLE 2-continued

Mean yield, grade index and nicotine of check cultivars an AOB 175 grown at the Pinhalzinho/SC and Vila Maria/RS, Brazil, during the 2004/05 crop season.

| Variety | Yield (Kg/ha) | Grade Index | Nicotine (%) |
|---|---|---|---|
| Vila Maria/Rio Grande do Sul | | | |
| TN 90 | 3,164 a | 68.3 a | 5.77 a |
| LI BY 21 | 2,501 b | 51.6 b | 3.08 b |
| AOB 175 | 2,692 b | 65.2 a | 3.31 b |
| AVERAGE CROP 2004/05 | | | |
| TN 90 | 3,238 a | 63.9 a | 5.52 a |
| LI BY 21 | 2,725 b | 50.5 b | 2.84 b |
| AOB 175 | 2,938 b | 56.6 ab | 2.98 b |

Table 3 presents data from the 2005/2006 crop season. Experiments were conducted at three different locations in Brazil: Palmitos/Santa Catarina, Pinhalzinho/Santa Catarina and Anta Gorda/Rio Grande do Sul (Latitude: 28°53'41"S; Longitude: 52°02'09"W). The experiments followed the same design as set forth above for the 2004/2005 growing season, except that the plot size changed from 44 to 30 plants/plot. The total nitrogen used was 224, 212 and 248 kg/ha, respectively. Harvesting took place at 48, 41 and 53 days after topping, respectively.

TABLE 3

Mean yield, grade index and nicotine of check cultivars and AOB 175 grown at Palmitos/SC, Pinhalzinho/SC and Anta Gorda/RS, Brazil, during the 2005/06 crop season.

| Variety | Yield (Kg/ha) | Grade Index | Nicotine (%) |
|---|---|---|---|
| Palmitos/Santa Catarina | | | |
| TN 90 | 3,588 a* | 70.3 a | 5.79 a |
| LI BY 21 | 2,766 a | 57.9 a | 3.29 b |
| AOB 175 | 3,269 a | 53.0 a | 3.64 b |
| Pinhalzinho/Santa Catarina | | | |
| TN 90 | 2,813 a | 71.9 a | 5.62 a |
| LI BY 21 | 2,661 a | 62.4 a | 2.14 b |
| AOB 175 | 2,865 a | 64.4 a | 2.96 b |
| Anta Gorda/Rio Grande do Sul | | | |
| TN 90 | 3,049 a | 79.8 a | 5.74 a |
| LI BY 21 | 2,546 a | 77.4 a | 2.86 b |
| AOB 175 | 2,884 a | 73.1 a | 3.82 ab |
| AVERAGE CROP 2005/06 | | | |
| TN 90 | 3,150 a | 74.0 a | 5.72 a |
| LI BY 21 | 2,658 a | 65.9 a | 2.76 b |
| AOB 175 | 3,006 a | 63.5 a | 3.48 b |

During the 2006/2007 crop season, an experiment was conducted Vera Cruz/Rio Grande do Sul, Brazil (Latitude: 29°42'53"S; Longitude: 52°30'20"W) to evaluate nicotine and total of nitrogen of the new variety, AOB 175, as compared to the parental varieties, TN 90 and LI BY 21. These data are shown in Table 4.

TABLE 4

Mean total alkaloids and total nitrogen of check cultivars and AOB 175, grown in the Research Center of Alliance One, Vera Cruz/RS, Brazil, during the 2006/07 crop season.

| Variety | Nicotine (%) | Total Nitrogen (%) |
|---|---|---|
| TN 90 | 5.55 a* | 4.23 a |
| LI BY 21 | 3.31 b | 3.57 a |
| AOB 175 | 3.22 b | 3.49 a |

As shown in Tables 2, 3 and 4, the nicotine levels of the new variety AOB 175 were determined to be significantly lower than that for TN 90 but similar to LI BY 21. In contrast, the total nitrogen content of all three varieties was similar (Table 4). The average yield for AOB 175 over both crop seasons and all growing sites was generally intermediate to, but not statistically different from either parent, TN 90 or LI BY 21 (Tables 2 and 3). In the 2004/2005 crop season, the average grade index for AOB 175 was lower than TN 90 and similar to LI BY 21 (Table 2), but during the 2005/2006 crop season, yield and grade index were similar for all three varieties (Table 3).

Thus, the new tobacco variety AOB 175 shows different phenotypic characteristics when compared to its progenitors, TN 90 and LI BY 21. Of significance, and as discussed above, AOB 175 produces less nicotine than the parent, TN 90. Specifically, AOB 175 produces about 40 to 45% less nicotine compared with TN 90. In addition, AOB 175 can be distinguished from TN 90 by its susceptibility to Potato Virus Y (PVY), whereas TN 90 is resistant.

Further, when compared with LI BY 21, another important distinctive characteristic of AOB 175 is the rate of maturation with AOB 175 maturing about 15 days later than LI BY 21. Additionally, the untopped plant height of AOB 175 is approximately 25 cm greater than LI BY 21. The leaves of AOB 175 are about the same width as those of LI BY 21, but average about 5 cm longer. Also, AOB 175 has a more consistent leaf size and shape than LI BY 21. The leaf insertion angle for AOB 175 is similar to LI BY 21. In untopped plants, AOB 175 averages five leaves more than LI BY 21. Additionally, the leaf surface is of AOB 175 is puckered (Exhibit C—Class 2) while that of LI BY 21 is smooth (Exhibit C—Class 1). The AOB 175 leaf margin is wavy (Exhibit C—Class 1) whereas LI BY 21, has a leaf margin that is not wavy (Exhibit C—Class 2). AOB 175 is overall a more compact plant than LI BY 21, thus allowing for less damage during harvest. In addition, AOB 175 tolerates colder climates better than LI BY 21.

When comparing AOB 175 with its sister lines, AOB 174 and AOB 176, AOB 175 is the latest maturing, being about 5 days later than AOB 174 and 10 days later than AOB 176. In untopped plants, AOB 175 is 5 cm taller than AOB 174 and 20 cm taller than AOB 176. The leaf size of AOB 175 is intermediate to its two sister lines, being about 2 cm broader and 5 cm longer than AOB 174 and 2 cm narrower and 2 cm shorter than AOB 176. The leaf insertion angle for AOB 175 is similar to AOB 174, but is larger than AOB 176. Compared with its sister lines, AOB 175 averages five more leaves in untopped plants than AOB 176 and about three more leaves than AOB 174. The leaf surface of AOB 175 is puckered (Exhibit C—Class 2) while the leaf surface of AOB 174 is smooth (Exhibit C—Class 1). In addition, AOB 175 has a leaf margin that is wavy (Exhibit C—Class 1), similar to AOB 174, but different from AOB 176, which is not wavy (Exhibit C—Class 2).

Thus, AOB 175 is a new and distinct tobacco variety, differing from both parental varieties, TN 90 and LI BY 21, and from its sister lines, AOB 174 and AOB 176. AOB 175, with similar yield and quality to TN 90, provides the additional advantage over TN 90 of producing less nicotine and thus, is a good alternative for producing tobacco with less nicotine content. In addition, compared with its sister lines, AOB 174 and AOB 176, AOB 175 is appropriate for growing in a normal season mainly due to its intermediate maturation rate and leaf number.

Table 5 provides a comparison of various characteristics of the new variety AOB 175 with those of the known tobacco varieties Kentucky 14 (KY 14) and Burley 21 (BY 21).

TABLE 5

Comparison of AOB 175 with the tobacco varieties BY 21 and KY 14.

| Characteristic | Variety | | |
|---|---|---|---|
| | AOB 175 | BY 21 | KY 14 |
| Maturity-Flowering | 83 | 68 | 73 |
| Plant Height (cm) | | | |
| Topped | 163 | 128 | 144 |
| Not Topped | 206 | 179 | 184 |
| Leaf Length | | | |
| 5th leaf | 64 | 62.6 | 62.2 |
| 10th leaf | 66 | 61.6 | 67.8 |
| 15th leaf | 63.4 | 56.8 | 65.8 |
| Leaf Width (cm) | | | |
| 5th leaf | 31 | 33 | 34.8 |
| 10th leaf | 30.6 | 29.2 | 34 |
| 15th leaf | 28 | 26 | 27.2 |
| Leaf Angle (degrees) | | | |
| 5th leaf | 77 | 81 | 48 |
| 10th leaf | 72 | 65 | 47 |
| 15th leaf | 62 | 60 | 56 |
| Leaf Number per plant | | | |
| Topped Normal | 21.6 | 20.4 | 21.8 |
| Not Topped | 25.8 | 21.6 | 24 |
| Internode Length (mm) | 46 | 48 | 54 |
| % Nicotine | 3.66 | | 5.12 |
| % Nor Nicotine | 0.08 | | 0.09 |
| % Total Nitrogen | 3.49 | | 3.92 |

The goal of this TN 90 and LI BY 21 cross was to develop a new variety with low to intermediate nicotine content and with agronomic and smoking characteristics desirable to farmers and to the tobacco industry. Thus, the AOB 175 variety shows TMV resistance, high yield and quality with lower nicotine levels than that observed for the parental variety, TN 90.

Accordingly, one aspect of the present invention is a tobacco seed designated AOB 175. Another aspect of the invention is a tobacco plant, or a part thereof, produced by the seed of the tobacco cultivar AOB 175. A further aspect of the invention is pollen or an ovule of a tobacco plant produced by the seed of AOB 175. In addition, the present invention provides a tobacco plant, or a part thereof, produced by the seed of AOB 175, wherein the tobacco plant further comprises a nucleic acid conferring male sterility.

The present invention additionally provides a tobacco plant, or a part thereof, having all the physiological and morphological characteristics of tobacco cultivar AOB 175. In other aspects of the invention, the tobacco plant, or a part thereof, having all the physiological and morphological characteristics of tobacco cultivar AOB 175, further comprises a nucleic acid conferring male sterility.

Still further, the invention provides a tissue culture of regenerable cells of the plant, or part thereof, of the present invention, which culture regenerates tobacco plants capable of expressing all the morphological and physiological characteristics of tobacco cultivar AOB 175. The regenerable cells of the invention include but are not limited to cells from leaves, pollen, embryos, cotyledons, hypocotyls, roots, root tips, anthers, flowers and a part thereof, ovules, shoots, stems, stalks, pith and capsules or callus or protoplasts derived therefrom. Thus, another aspect of this invention is to provide cells, which upon growth and differentiation produce tobacco plants having the physiological and morphological characteristics of tobacco cultivar AOB 175. In some embodiments, cells of cultivar AOB 175 are transformed genetically, for example with one or more nucleic acids described below, and transgenic plants of tobacco cultivar AOB 175 are regenerated therefrom.

AOB 175 has shown uniformity and stability within the limits of environmental influence for all the traits as described in the Variety Description Information (Table 1). A sufficient number of generations have been observed with careful attention paid to uniformity of plant type to ensure the homozygosity and phenotypic stability necessary for use in commercial hybrid seed production. No variant traits have been observed or are expected in AOB 175.

Other Embodiments of the Invention

The present invention also encompasses hybrid plants produced from tobacco cultivar AOB 175, tobacco plants derived from AOB 175, and AOB 175 plants comprising a nucleic acid that has been introduced therein by traditional breeding or genetic engineering techniques, and seeds, plant parts, and tissue cultures of the foregoing plants, as well as methods of producing the plants of the invention.

Accordingly, methods for crossing the tobacco plants of the present invention are provided. Such methods may comprise crossing the plant of the present invention, AOB 175, with itself or a second tobacco plant. The present invention further encompasses a method for producing hybrid tobacco seed, the method comprising crossing two tobacco plants and harvesting the resultant hybrid tobacco seed, wherein at least one tobacco plant is the tobacco plant of the present invention, AOB 175. In another embodiment, a method for producing a first generation ($F_1$) hybrid tobacco seed is provided comprising crossing the plant of the present invention with a different tobacco plant and harvesting the resultant first generation ($F_1$) hybrid tobacco seed. Further provided by the present invention are plants produced by these methods.

Additionally provided herein, is a method for producing an AOB 175-derived tobacco plant comprising: (a) crossing tobacco cultivar AOB 175 with a second tobacco plant to yield progeny tobacco seed; (b) growing said progeny tobacco seed, under plant growth conditions, to yield said AOB 175-derived tobacco plant. The method may still further comprise: a) crossing said AOB 175-derived tobacco plant with itself or another tobacco plant to yield additional AOB 175-derived progeny tobacco seed; (b) growing said progeny tobacco seed of step (a) under plant growth conditions, to yield additional AOB 175-derived tobacco plants; and (c) repeating the crossing and growing steps of (a) and (b) multiple times to generate further AOB 175-derived tobacco plants. In some embodiments, the crossing and growing steps of (a) and (b) in step (c) are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate further AOB 175-derived tobacco plants. In other embodiments, the crossing and growing steps of (a) and (b) in step (c) are repeated from 0 to n times in order to generate further AOB 175-derived tobacco plants. The invention further provides plants produced by these methods. Accordingly, the invention encompasses progeny plants and parts thereof with at least one ancestor that is hybrid tobacco plant AOB 175 and more specifically where the pedigree of this progeny includes 1, 2, 3, 4, 5, 6, and/or 7 cross pollinations to a tobacco plant AOB 175 or a plant that has AOB 175 as a progenitor.

Other embodiments of the present invention include a method for producing a tobacco plant that contains in its genetic material one or more transgenes, comprising crossing the tobacco plant of the present invention with either a second plant of another tobacco line, or a non-transformed tobacco plant of the present invention, wherein progeny are produced, so that the genetic material of the progeny that result from the cross comprises the transgene(s) operably linked to one or more regulatory elements. In one aspect of the invention, the one or more transgene includes but is not limited to a nucleic acid conferring herbicide resistance, insect resistance, disease resistance and/or male sterility. Further provided by the present invention are plants produced by this method.

Further provided by the present invention is a method for developing a tobacco plant in a tobacco plant breeding program using plant breeding techniques, which include employing a tobacco plant of the present invention, or a part thereof, as the source of plant breeding material. Plant breeding techniques that can be used in the method include, but are not limited to, recurrent selection, backcrossing, pedigree breeding, restriction fragment length polymorphism enhanced selection, genetic marker enhanced selection, double haploid breeding, single seed descent, multiple seed descent, and/or transformation. Further provided herein are plants produced by this method.

Accordingly, any methods using the cultivar AOB 175 are part of this invention: selfing, backcrosses, hybrid production, crosses to populations, and the like. All plants produced using cultivar AOB 175 as a parent are within the scope of this invention including plants derived from the cultivar AOB 175. Advantageously, AOB 175 cultures used in crosses with other tobacco cultivars can be used to produce a first generation (F1) tobacco hybrid seed and plants with superior characteristics.

I. Male Sterile Plants

Tobacco can be bred by both self-pollination and cross-pollination techniques. Individual tobacco flowers have both male and female reproductive organs, and tobacco is naturally self-pollinating. It is known in the art that it is often advantageous to create male sterile/female fertile plants so that self-pollination can be controlled.

Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp.

A reliable method of controlling male fertility in plants offers the opportunity for improved plant breeding. This is especially true for development of tobacco hybrids, which typically relies upon some sort of male sterility system. There are several options for controlling male fertility available to breeders, such as: manual or mechanical emasculation, cytoplasmic male sterility, genetic male sterility, gametocides and the like. In one approach, alternate strips of two tobacco lines are planted in a field, and the male portions of flowers are removed from one of the lines (female). Providing that there is sufficient isolation from sources of foreign tobacco pollen, the emasculated plant will be fertilized only from the other line (male), and the resulting seed is therefore hybrid and will form hybrid plants.

The laborious, and occasionally unreliable, mechanical emasculation process can be avoided by using cytoplasmic male-sterile (CMS) lines. Plants of a CMS line are male sterile as a result of factors resulting from the cytoplasmic, as opposed to the nuclear, genome. Thus, this characteristic is inherited exclusively through the female parent in tobacco plants, since only the female provides cytoplasm to the fertilized seed. CMS plants are fertilized with pollen from another line that is not male-sterile. Pollen from the second line may or may not contribute genes that make the hybrid plants male-fertile.

Alternative approaches of conferring genetic male sterility are also suitable, such as multiple mutant nucleic acids at separate locations within the genome that confer male sterility and chromosomal translocations.

Still further methods of conferring genetic male sterility use a variety of approaches such as delivering into the plant a nucleic acid encoding a cytotoxic substance associated with a male tissue specific promoter or an antisense system in which a nucleic acid critical to male fertility is identified and an antisense to that nucleic acid is inserted in the plant.

Another system useful in controlling male fertility makes use of gametocides. Gametocides do not involve a genetic system, but rather a topical application of chemicals. These chemicals affect cells that are critical to male fertility. The application of these chemicals affects fertility in the plants only for the growing season in which the gametocide is applied (see U.S. Pat. No. 4,936,904). Application of the gametocide, timing of the application and genotype specificity often limit the usefulness of the approach.

II. Hybrid Production

The use of male sterile lines is one factor in the production of tobacco hybrids. The development of tobacco hybrids involves, in general, the development of completely homozygous lines, the crossing of these lines, and the evaluation of the crosses. In the case of tobacco, a completely homozygous line may be an inbred or a doubled-haploid line.

Pedigree breeding and recurrent selection breeding methods are typically used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines or doubled-haploid lines, and the hybrids from these crosses are evaluated to determine which have commercial potential.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations, the heterozygous condition gives way to homogeneous lines as a result of self-pollination and selection. Typically in the pedigree method of breeding, five or more generations of selfing and selection is practiced. Thus, multiple crossings and growing steps may be carried out in order to generate a desired hybrid.

A single cross tobacco hybrid results from the cross of two tobacco lines (e.g., inbred or doubled-haploid lines), each of the parents having a genotype that complements the genotype of the other. The hybrid progeny of the first generation is designated $F_1$. Preferred $F_1$ hybrids may be more vigorous than either parent in a cross between inbred parents. This hybrid vigor, or heterosis, can be manifested in many polygenic traits, including increased vegetative growth and increased yield.

In general, the development of a tobacco hybrid involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). A consequence of the homozygosity and homogeneity of the inbred lines is that the hybrid between a defined pair of inbreds/doubled-haploids will always be the same. Once the parents that give a superior hybrid have been identified, the hybrid seed can be reproduced indefinitely as long as the homogeneity of the parents is maintained.

A single cross hybrid is produced when two lines are crossed to produce the $F_1$ progeny. A double cross hybrid is produced from four inbred lines crossed in pairs (A×B and C×D) and then the two $F_1$ hybrids are crossed again (A×B)× (C×D). Much of the hybrid vigor exhibited by $F_1$ hybrids is generally lost in the next generation ($F_2$). Consequently, seed from hybrids is not typically used for planting stock.

As described above, hybrid seed production regimes generally use male sterile/female fertile parent plants. Incomplete removal or inactivation of the pollen provides the potential for self pollination. This inadvertently self pollinated seed may be unintentionally harvested and packaged with hybrid seed. Once the seed is planted, it is possible to identify and select these self pollinated plants due to their decreased vigor. These self-pollinated plants will be genetically equivalent to the female inbred line used to produce the hybrid. Female selfs are identified by their less vigorous appearance for vegetative and/or reproductive characteristics as is known in the art.

Identification of these self-pollinated lines can also be accomplished through molecular marker analyses. Through these technologies, the homozygosity of the self-pollinated line can be verified by analyzing allelic composition at various loci along the genome.

III. Evaluation of Plants for Homozygosity and Phenotypic Stability

It is desirable and advantageous for a tobacco cultivar to be highly homogeneous, homozygous and phenotypically uniform and stable for use as a commercial cultivar. In the case of inbreds or other lines, there are many analytical methods available to determine the homozygotic and phenotypic stability of the variety.

The oldest and most traditional method of analysis is the observation of phenotypic traits. The data are usually collected in field experiments over the life of the tobacco plants to be examined. Phenotypic characteristics most often observed are for traits associated with seed yield, disease resistance, maturity, plant height, internode distance, flower color, leaf color, leaf yield, leaf size, leaf angle, lamina-midrib ratio, and concentration of chemical components such as nicotine, total alkaloids or reducing sugars.

In addition to phenotypic observations, the genotype of a plant can also be examined. There are many laboratory-based techniques available for the analysis, comparison and characterization of plant genotypes; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The presence or absence of a marker in the plant genotype may be determined by any method known in the art. For example, the marker sequence (or its complement) may be used as a hybridization probe, e.g., for Southern or in situ analysis of genomic DNA. Typically, however, due to greater ease and sensitivity, an amplification method, such as PCR will be used to detect the presence or absence of the marker in the plant genotype.

Molecular markers can be used in any method of nucleic acid amplification known in the art. Such methods include but are not limited to Polymerase Chain Reaction (PCR; described in U.S. Pat. Nos. 4,683,195; 4,683,202; 4,800,159; 4,965,188), Strand Displacement Amplification (SDA; described by G. Walker et al., *Proc. Nat. Acad. Sol. USA* 89: 392 (1992); G. Walker et al., *Nucl. Acids Res.* 20: 1691 (1992); U.S. Pat. No. 5,270,184), thermophilic Strand Displacement Amplification (tSDA; EP 0 684 315 to Frasier et al.), Self-Sustained Sequence Replication (3SR; J. C. Guatelli et al., *Proc Natl. Acad. Sci. USA* 87: 1874-78 (1990)), Nucleic Acid Sequence-Based Amplification (NASBA; U.S. Pat. No. 5,130,238 to Cangene), the Qβ replicase system (P. Lizardi et al., *BioTechnology* 6: 1197 (1988)), or transcription based amplification (D. Y. Kwoh et al., *Proc. Natl. Acad. Sci. USA* 86: 1173-77 (1989)).

IV. Transfer of Traits into Tobacco Cultivar AOB 175

Genetic variants of AOB 175 that are naturally-occurring or created through traditional breeding methods using cultivar AOB 175 are also intended to be within the scope of this invention. In particular embodiments, the invention encompasses plants of cultivar AOB 175 and parts thereof further comprising one or more additional traits, in particular, specific, single gene transferred traits. Examples of traits that may be transferred include, but are not limited to, herbicide resistance, disease resistance (e.g., bacterial fungal or viral disease), nematode resistance, tolerance to abiotic streses (e.g., drought, temperature, salinity), yield enhancement, improved nutritional quality (e.g., oil starch and protein content or quality), altered chemical composition (e.g., nicotine, secondary alkaloids, total alkaloids, reducing sugars), improved leaf characteristics (color, shape, size, number, angle), altered reproductive capability (e.g., male sterility) or other agronomically important traits.

Such traits may be introgressed into cultivar AOB 175 from another tobacco cultivar or may be directly transformed into cultivar AOB 175 (discussed below). One or more new traits can be transferred to cultivar AOB 175, or, alternatively, one or more traits of cultivar AOB 175 are altered or substituted. The introgression of the trait(s) into cultivar AOB 175 may be achieved by any method of plant breeding known in the art, for example, pedigree breeding, backcrossing, doubled-haploid breeding, and the like (see, Wernsman, E. A., and Rufty, R. C. 1987. Chapter Seventeen. Tobacco. Pages 669-698 In: *Cultivar Development. Crop Species*. W. H. Fehr (ed.), MacMillan Publishing Co., Inc., New York, N.Y. 761 pp.).

The laboratory-based techniques described above, in particular RFLP and SSR, can be used in such backcrosses to identify the progenies having the highest degree of genetic identity with the recurrent parent. This permits one to accelerate the production of tobacco cultivars having at least 90%, preferably at least 95%, more preferably at least 99% genetic identity with the recurrent parent, yet more preferably genetically identical to the recurrent parent, and further comprising the trait(s) introgressed from the donor parent. Such determination of genetic identity can be based on molecular markers used in the laboratory-based techniques described above.

The last backcross generation can be selfed to give pure breeding progeny for the nucleic acid(s) being transferred. The resulting plants generally have essentially all of the morphological and physiological characteristics of cultivar AOB 175, in addition to the transferred trait(s) (e.g., one or more single gene traits). The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred.

Those skilled in the art will appreciate that the tobacco nucleic acids described below in connection with tobacco plants produced by genetic engineering techniques may also be introduced into cultivar AOB 175 by conventional breeding methods.

V. Transformation of Tobacco

With the advent of molecular biological techniques that have allowed the isolation and characterization of nucleic acids that encode specific protein products, scientists in the field of plant biology developed a strong interest in engineering the genome of plants to contain and express foreign nucleic acids, or additional, or modified versions of native or endogenous nucleic acids (perhaps driven by different promoters) in order to alter the traits of a plant in a specific manner. Such foreign, additional and/or modified nucleic acids are referred to herein collectively as "transgenes." The term "transgene," as used herein, is not necessarily intended to indicate that the foreign nucleic acid is from a different plant species. For example, the transgene may be a particular allele derived from another tobacco line or may be an additional copy of an endogenous gene. Over the last twenty to twenty-five years several methods for producing transgenic plants have been developed. Therefore, in particular embodiments, the present invention also encompasses transformed versions of the tobacco cultivar AOB 175.

Plant transformation generally involves the construction of an expression vector that will function in plant cells. Such a vector comprises DNA or RNA comprising a nucleic acid under control of, or operatively linked to, a regulatory element (for example, a promoter). The expression vector may contain one or more such operably linked nucleic acid/regulatory element combinations. The vector(s) may be in the form of, for example, a plasmid or a virus, and can be used, alone or in combination with other vectors, to provide transformed tobacco plants, using transformation methods as described below to incorporate transgenes into the genetic material of the tobacco plant(s).

Any transgene(s) known in the art may be introduced into a tobacco plant, tissue, cell or protoplast according to the present invention, e.g., to improve commercial or agronomic traits, herbicide resistance, disease resistance (e.g., to a bacterial fungal or viral disease), insect resistance, nematode resistance, yield enhancement, nutritional quality (e.g., oil starch and protein content or quality), leaf characteristics (color, shape, size, number, angle), and altered reproductive capability (e.g., male sterility) or chemical composition (e.g., nicotine, total alkaloids, reducing sugars). Alternatively, a transgene may be introduced for the production of recombinant proteins (e.g., enzymes) or metabolites.

In particular embodiments of the invention a transgene conferring herbicide resistance, insect resistance, or disease resistance is introduced into the tobacco plant. Alternatively, a transgene conferring male sterility is introduced.

A. Expression Vectors For Tobacco Transformation.

1. Genetic Markers.

Expression vectors typically include at least one genetic marker, operably linked to a regulatory element (a promoter, for example) that allows transformed cells containing the marker to be either recovered by negative selection, i.e., inhibiting growth of cells that do not contain the selectable marker, or by positive selection, i.e., screening for the product encoded by the genetic marker. Many commonly used selectable marker for plant transformation are well known in the transformation art, and include, for example, nucleic acids that code for enzymes that metabolically detoxify a selective chemical agent which may be an antibiotic or a herbicide, or nucleic acids that encode an altered target which is insensitive to the inhibitor. A few positive selection methods are also known in the art.

One commonly used selectable marker for plant transformation is neomycin phosphotransferase II (npfII), isolated from transposon Tn5, which when placed under the control of plant regulatory signals confers resistance to kanamycin (Fraley et al., (1983) *Proc. Natl. Acad. Sci. U.S.A.* 80: 4803). Another commonly used selectable marker is hygromycin phosphotransferase, which confers resistance to the antibiotic hygromycin (Vanden Elzen et al., (1985) *Plant Mol. Biol.* 5: 299).

Additional selectable markers of bacterial origin that confer resistance to antibiotics include gentamycin acetyl transferase, streptomycin phosphotransferase, aminoglycoside-3'-adenyl transferase, the bleomycin resistance determinant (Hayford et al., (1988) *Plant Physiol.* 86: 1216; Jones et al., (1987) *Mol. Gen. Genet.,* 210: 86; Svab et a/., (1990) *Plant Mol. Biol.* 14: 197; Hille et al., (1986) *Plant Mol. Biol.* 7: 175). Other selectable markers confer resistance to herbicides such as glyphosate, glufosinate or bromoxynil (Comai et al., (1985) *Nature* 317: 741; Gordon-Kamm et al., (1990) *Plant Cell* 2: 603; and Stalker et al., (1988) *Science* 242: 419).

Selectable markers for plant transformation that are not of bacterial origin include, for example, mouse dihydrofolate reductase, plant 5-eno/pyruvylshikimate-3-phosphate synthase and plant acetolactate synthase (Eichholtz et al., (1987) *Somatic Cell Mol. Genet.* 13: 67; Shah et al., (1986) *Science* 233: 478; Charest et al., (1990) *Plant Cell Rep.* 8: 643).

Another class of markers for plant transformation requires screening of presumptively transformed plant cells rather than direct genetic selection of transformed cells for resistance to a toxic substance such as an antibiotic. These markers are particularly useful to quantify or visualize the spatial pattern of expression in specific tissues and are frequently referred to as reporters because they can be fused to a nucleic acid or regulatory sequence for the investigation of nucleic acid expression. Commonly used reporters for screening presumptively transformed cells include β-glucuronidase (GUS), β-galactosidase, luciferase and chloramphenicol acetyltransferase (Jefferson, R. A., (1987) *Plant Mol. Biol. Rep.* 5: 387; Teeri et al., (1989) *EMBO J* 8: 343; Koncz et al., (1987) *Proc. Natl. Acad. Sci. U.S.A.* 84:131; De Block et al., (1984) *EMBO J.* 3: 1681).

In vivo methods for visualizing GUS activity that do not require destruction of plant tissue are also available (Molecular Probes Publication 2908, Imagene Green™, p. 1-4 (1993) and Naleway et al., (1991) *J. Cell Biol.* 115: 15). However, these in vivo methods for visualizing GUS activity have not proven useful for recovery of transformed cells because of low sensitivity, high fluorescent backgrounds, and limitations associated with the use of luciferase as a selectable marker.

In addition, a nucleic acid encoding Green Fluorescent Protein (GFP) has been utilized as a marker for nucleic acid expression in prokaryotic and eukaryotic cells (Chalfie et al., (1994) *Science* 263: 802). GFP and mutants of GFP may be used as screenable markers.

2. Promoters.

Nucleic acids included in expression vectors are typically driven by a nucleotide sequence comprising a regulatory element, for example, a promoter. Several types of promoters are now well known in the transformation art, as are other regulatory elements that can be used alone or in combination with promoters.

As used herein, the term "promoter" refers to a region of a nucleotide sequence that incorporates the necessary signals for the efficient expression of a coding sequence. This may include sequences to which an RNA polymerase binds, but is not limited to such sequences and can include regions to which other regulatory proteins bind together with regions involved in the control of protein translation and can also include coding sequences. A "plant promoter" is a promoter capable of initiating transcription in plant cells. Such promoters include those that drive expression of a nucleotide sequence constitutively, those that drive expression when induced, and those that drive expression in a tissue- or developmentally specific manner, as these various types of promoters are known in the art.

(A) Constitutive Promoters.

Thus, for example, in some embodiments of the invention, a constitutive promoter can be used to drive the expression of a transgene in a plant cell. A constitutive promoter is an unregulated promoter that allows for continual transcription of its associated coding sequence. Thus, constitutive promoters are generally active under most environmental conditions, in most or all cell types and in most or all states of development or cell differentiation.

Any constitutive promoter functional in a plant can be utilized in the instant invention. Exemplary constitutive promoters include, but are not limited to, the promoters from plant viruses including, but not limited to, the 35S promoter from CaMV (Odell et al., *Nature* 313: 810(1985)); figwort mosaic virus (FMV) 35S promoter (P-FMV35S, U.S. Pat. Nos. 6,051,753 and 6,018,100); the enhanced CaMV35S promoter (e35S); the 1'- or 2'-promoter derived from T-DNA of *Agrobacterium tumefaciens*; the nopaline synthase (NOS) and/or octopine synthase (OCS) promoters, which are carried on tumor-inducing plasmids of *Agrobacterium tumefaciens* (Ebert et al., Proc. Natl. Acad. Sci. (U.S.A.), 84:5745 5749, 1987); actin promoters including, but not limited to, rice actin (McElroy et al., *Plant Cell* 2: 163 (1990); U.S. Pat. No. 5,641,876); histone promoters; tubulin promoters; ubiquitin and polyubiquitin promoters ((Sun and Callis, Plant J., 11(5): 1017-1027 (1997)); Christensen et al., *Plant Mol. Biol* 12: 619 (1989) and Christensen et al., *Plant Mol. Biol.* 18: 675 (1992)); pEMU (Last et al., *Theor. Appl. Genet.* 81: 581

(1991)); the mannopine synthase promoter (MAS) (Velten et al., *EMBO J.* 3: 2723(1984)); maize H3 histone (Lepelit et al., *Mol. Gen. Genet.* 231: 276 (1992) and Atanassova et al., *Plant Journal* 2: 291 (1992)); the ALS promoter, a XbaI/NcoI fragment 5' to the *Brassica napus* ALS3 structural gene (or a nucleotide sequence that has substantial sequence similarity to said Xbal/NcoI fragment); ACT11 from *Arabidopsis* (Huang et al., *Plant Mol. Biol.* 33:125-139 (1996)); Cat3 from Arabidopsis (GenBank No. U43147, Zhong et al., *Mol. Gen. Genet.* 251:196-203 (1996)); GPc1 from maize (GenBank No. X15596, Martinez et al., *J. Mol. Biol.* 208:551-565 (1989)); and Gpc2 from maize (GenBank No. U45855, Manjunath et al., *Plant Mol. Biol.* 33:97-112 (1997)).

(B) Inducible Promoters.

In some embodiments of the present invention, an inducible promoter can be used to drive the expression of a transgene. Inducible promoters activate or initiate expression only after exposure to, or contact with, an inducing agent. Inducing agents include, but are not limited to, various environmental conditions (e.g., pH, temperature), proteins and chemicals. Examples of environmental conditions that can affect transcription by inducible promoters include pathogen attack, anaerobic conditions, extreme temperature and/or the presence of light. Examples of chemical inducing agents include, but are not limited to, herbicides, antibiotics, ethanol, plant hormones and steroids. Any inducible promoter that is functional in a plant can be used in the instant invention (see, Ward et al., (1993) *Plant Mol. Biol.* 22: 361 (1993)). Exemplary inducible promoters include, but are not limited to, that from the ACEI system, which responds to copper (Melt et al., *PNAS* 90: 4567 (1993)); the In2 nucleic acid from maize, which responds to benzenesulfonamide herbicide safeners (Hershey et al., (1991) *Mol. Gen. Genetics* 227: 229 (1991) and Gatz et al., *Mol. Gen. Genetics* 243: 32 (1994)); a heat shock promoter, including, but not limited to, the soybean heat shock promoters Gmhsp 17.5-E, Gmhsp 17.2-E and Gmhsp 17.6-L and those described in U.S. Pat. No. 5,447,858; the Tet repressor from Tn10 (Gatz et al., *Mol. Gen. Genet.* 227: 229 (1991)) and the light-inducible promoter from the small subunit of ribulose bisphosphate carboxylase (ssRUBISCO). Other examples of inducible promoters include, but are not limited to, those described by Moore et al. (*Plant J.* 45:651-683 (2006)). Additionally, some inducible promoters respond to an inducing agent to which plants do not normally respond. An example of such an inducible promoter is the inducible promoter from a steroid hormone gene, the transcriptional activity of which is induced by a glucocorticosteroid hormone (Schena et al., *Proc. Natl. Acad. Sci. U.S.A.* 88: 421 (1991)).

(C) Tissue-Specific or Tissue-Preferred Promoters.

In further embodiments of the present invention, a tissue-specific promoter can be used to drive the expression of a transgene in a particular tissue in the transgenic plant. Tissue-specific promoters drive expression of a nucleic acid only in certain tissues or cell types, e.g., in the case of plants, in the leaves, stems, flowers and their various parts, roots, fruits and/or seeds, etc. Thus, plants transformed with a nucleic acid of interest operably linked to a tissue-specific promoter produce the product encoded by the transgene exclusively, or preferentially, in a specific tissue or cell type.

Any plant tissue-specific promoter can be utilized in the instant invention. Exemplary tissue-specific promoters include, but are not limited to, a root-specific promoter, such as that from the phaseolin gene (Murai et al., (1983) *Science* 23: 476 and Sengupta-Gopalan et al., (1985) *Proc. Natl. Acad. Sci. USA* 82: 3320); a leaf-specific and light-induced promoter such as that from cab or rubisco (Simpson et al. (1985) *EMBO J.* 4: 2723 and Timko et al., (1985) *Nature* 318: 579); the fruit-specific E8 promoter from tomato (Lincoln et al. *Proc. Nat'l. Acad. Sci. USA* 84: 2793-2797 (1988); Deikman et al. EMBO J. 7: 3315-3320 (1988); Deikman et al. *Plant Physiol.* 100: 2013-2017 (1992); seed-specific promoters of, for example, *Arabidopsis thaliana* (Krebbers et al. (1988) *Plant Physiol.* 87:859); an anther-specific promoter such as that from LAT52 (Twell et al. (1989) *Mol. Gen. Genet.* 217: 240) or European Patent Application No 344029, and those described by Xu et al. (*Plant Cell Rep.* 25:231-240 (2006)) and Gomez et al. (*Planta* 219:967-981 (2004)); a pollen-specific promoter such as that from Zm13 (Guerrero et al., (1993) *Mol. Gen. Genet.* 224: 161), and those described by Yamaji et al. (*Plant Cell Rep.* 25:749-57 (2006)) and Okada et al. (*Plant Cell Physiol.* 46:749-802 (2005)); a pith-specific promoter, such as the promoter isolated from a plant TrpA gene as described in International PCT Publication No. WO93/07278; and a microspore-specific promoter such as that from apg (Twell et al. (1993) *Sex. Plant Reprod.* 6: 217). Exemplary green tissue-specific promoters include the maize phosphoenol pyruvate carboxylase (PEPC) promoter, small subunit ribulose bis-carboxylase promoters (ssRUBISCO) and the chlorophyll a/b binding protein promoters.

3. Signal Sequences For Targeting Proteins to Subcellular Compartments.

Transport of proteins produced by transgenes to a subcellular compartment such as the chloroplast, vacuole, peroxisome, glyoxysome, cell wall or mitochondrion, or for secretion into the apoplast, may be accomplished by means of operably linking a nucleotide sequence encoding a signal sequence typically at the 5' and/or 3' region of a sequence encoding the protein of interest. Association of targeting sequences with the coding sequence may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art (see, for example, Becker et al., (1992) *Plant Mol. Biol.*20: 49; Close, P. S., Master's Thesis, Iowa State University (1993); Knox, C., et al., (1987) *Plant Mol. Biol.* 9: 3; Lerner et al., (1989) *Plant Physiol.* 91: 124; Fontes et al., (1991) *Plant Cell* 3: 483; Matsuoka et al., (1991) *Proc. Natl. Acad. Sci.* 88: 834; Gould et al., (1989) *J. Cell Biol* 108: 1657; Creissen et al., (1991) *Plant J.* 2: 129; Kalderon et al., (1984) *Cell* 39: 499; Stiefel et al., (1990) *Plant Cell* 2: 785).

B. Foreign Nucleic Acids that May be Introduced into Tobacco Plants.

With transgenic plants according to the present invention, a foreign protein can be produced in commercial quantities. Thus, techniques for the selection and propagation of transformed plants, which are well understood in the art, yield a plurality of transgenic plants, which are harvested in a conventional manner, and a foreign protein can then be extracted from a tissue of interest or from total biomass. Protein extraction from plant biomass can be accomplished by known methods which are discussed, for example, by Heney and Orr, (1991) *Anal. Biochem.* 114: 92.

According to embodiments of the invention, a transgenic tobacco plant is provided for commercial production of foreign protein. A genetic map can be generated, for example, via conventional Restriction Fragment Length Polymorphisms (RFLP), Polymerase Chain Reaction (PCR) analysis, and Simple Sequence Repeats (SSR), which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, nucleic acids of agronomic importance can be expressed in transformed plants. More particularly, plants can be genetically engineered to express various phenotypes of agronomic interest. Exemplary nucleic acids implicated in this regard include, but are not limited to, those described below.

As an example, a nucleic acid conferring male sterility may be transformed into cultivar AOB 175. There are several methods of conferring genetic male sterility available, such as multiple mutant nucleic acids at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. Examples include: (A) Introduction of a deacetylase nucleic acid under the control of a tapetum-specific promoter and with the application of the chemical N-Ac-PPT (WO 01/29237). (B) Introduction of various stamen-specific promoters (WO 92/13956, WO 92/13957). (C) Introduction of the barnase and the barstar nucleic acids (Paul et al. Plant Mol. Biol. 19:611 622,1992). For additional examples of nuclear male and female sterility systems and nucleic acids, see also, Nikova et al., *Plant Cell, Tissue and Organ Culture* 27:289-295 (1991); Nikova et al., *Euphytica* 94:375-378 (1997); Atanassov et al., *Theoretical and Applied Genetics* 97:982-985 (1998); Berbec, A. Bull. Spec. Coresta, Lisbon Congress, p.79, abstract AP30, (2000); U.S. Pat. No. 5,859,341; U.S. Pat. No. 6,297,426; U.S. Pat. No. 5,478,369; U.S. Pat. No. 5,824,524; U.S. Pat. No. 5,850,014; and U.S. Pat. No. 6,265,640; all of which are hereby incorporated by reference.

In an additional embodiment, a transgene whose expression results or contributes to a desired trait to be transferred to cultivar AOB 175 comprises a nucleic acid encoding an insecticidal protein, such as, for example, a crystal protein of *Bacillus thuringiensis* or a vegetative insecticidal protein from *Bacillus cereus*, such as VIP3 (see, for example, Estruch et al. (1997) *Nat Biotechnol* 15:137).

In a further embodiment, a transgene introduced into cultivar AOB 175 comprises a nucleic acid conferring herbicide tolerance whose expression renders plants of cultivar AOB 175 tolerant to the herbicide. For example, expression of an altered acetohydroxyacid synthase (AHAS) enzyme confers upon plants tolerance to various imidazolinone or sulfonamide herbicides (U.S. Pat. No. 4,761,373). In a still further embodiment, a nucleic acid conferring tolerance to imidazolinones or sulfonylurea herbicides is transferred into cultivar AOB 175. Expression of a mutant acetolactate synthase (ALS) will render the plants resistant to inhibition by sulfonylurea herbicides (U.S. Pat. No. 5,013,659).

U.S. Pat. No. 4,975,374 describes plant cells and plants containing a nucleic acid encoding a mutant glutamine synthetase (GS) which confers resistance to herbicides that are known to inhibit GS, e.g., phosphinothricin and methionine sulfoximine. In addition, expression of a Streptomyces bar nucleic acid encoding a phosphinothricin acetyl transferase results in tolerance to the herbicide phosphinothricin or glufosinate (U.S. Pat. No. 5,489,520). U.S. Pat. No. 5,162,602 discloses plants tolerant to inhibition by cyclohexanedione and aryloxyphenoxypropanoic acid herbicides. The tolerance is conferred by an altered acetyl coenzyme A carboxylase (ACCase). U.S. Pat. No. 5,554,798 discloses transgenic glyphosate tolerant plants, which tolerance is conferred by an altered 5-enolpyruvyl-3-phosphoshikimate (EPSP) synthase nucleic acid. In another particular embodiment, tolerance to a protoporphyrinogen oxidase inhibitor is achieved by expression of a tolerant protoporphyrinogen oxidase enzyme in plants (U.S. Pat. No. 5,767,373). In another particular embodiment, a nucleic acid transferred into cultivar AOB 175 comprises a transgene conferring tolerance to a herbicide and at least one other transgene conferring another trait, such as for example, insect resistance or tolerance to another herbicide.

Other illustrative transgenes are set forth below.

1. Transgenes that Confer Resistance to Pests or Disease and that Encode:

(A) Plant disease resistance. Plant defenses are often activated by specific interaction between the product of a nucleic acid coding for disease resistance gene (R) in the plant and the product of a corresponding nucleic acid coding for avirulence (Avr) in the pathogen. A plant variety can be transformed with a cloned nucleic acid conferring resistance in order to engineer plants that are resistant to specific pathogens (see, for example, Jones et al., (1994) *Science* 266: 789, cloning of the tomato Cf-9 gene for resistance to *Cladosporium fulvum*; Martin et al., (1993) *Science* 262: 1432, tomato Pto gene for resistance to *Pseudomonas syringae* pv.; Mindrinos et al., (1994) *Cell* 78: 1089, Arabidopsis RSP2 nucleic acid encoding resistance to *Pseudomonas syringae*).

(B) A *Bacillus thuringiensis* protein, a derivative thereof or a synthetic polypeptide modeled thereon (see, for example, Geiser et al., (1986) *Gene* 48: 109, disclosing the cloning and nucleotide sequence of Bt δ-endotoxin). Moreover, DNA molecules encoding δ-endotoxin can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and 10/606,320.

(C) A lectin (see, for example, the disclosure by Van Damme et al., (1994) *Plant Molec. Biol.* 24: 25), which discloses the nucleotide sequences of several *Clivia miniata* mannose-binding lectins.

(D) A vitamin-binding protein such as avidin (see PCT publication WO 93/06487). This publication teaches the use of avidin and avidin homologues as larvicides against insect pests.

(E) An enzyme inhibitor, for example, a protease inhibitor or an amylase inhibitor (see, for example, Abe et al., (1987) *J. Biol. Chem.* 262: 16793, nucleotide sequence of rice cysteine proteinase inhibitor; Huub et al., (1993) *Plant Molec.* 21: 985; nucleotide sequence of cDNA encoding tobacco proteinase inhibitor 1; and Sumitani et al., (1993) *Biosci. Biotech. Biochem.* 57: 1243, nucleotide sequence of *Streptomyces nitrosporeus* amylase inhibitor).

(F) An insect-specific hormone or pheromone such as an ecdysteroid or juvenile hormone, a variant thereof, a mimetic based thereon, or an antagonist or agonist thereof (see, for example, the disclosure of Hammock et al., (1990) *Nature*

344: 458, of baculovirus expression of cloned juvenile hormone esterase, an inactivator of juvenile hormone).

(G) An insect-specific peptide or neuropeptide which, upon expression, disrupts the physiology of the affected pest (for example, see the disclosures of Regan, (1994) *J. Biol. Chem.* 269: 9, expression cloning yields DNA coding for insect diuretic hormone receptor; Pratt et al., (1989) *Biochem. Biophys. Res. Comm.* 163: 1243, an allostatin is identified in *Diploptera puntata*). Chattopadhyay et al. (2004) *Crit. Rev. Microbiol.* 30 (1): 33 54 2004; Zjawiony (2004) *J. Nat. Prod.* 67 (2): 300 310; Carlini & Grossi-de-Sa (2002) *Toxicon,* 40 (11): 1515 1539; Ussuf et al. (2001) *Curr. Sci.* 80 (7): 847 853; and Vasconcelos & Oliveira (2004) *Toxicon* 44 (4): 385 403 See also U.S. Pat. No. 5,266,317 to Tomalski et al., which discloses nucleic acis encoding insect-specific, paralytic neurotoxins.

(H) An insect-specific venom produced in nature by a snake, a wasp, or the like (see, e.g., Pang et al., (1992) *Gene* 116: 165, for disclosure of heterologous expression in plants of a nucleic acid encoding a scorpion insectotoxic peptide).

(I) An enzyme responsible for an hyperaccumulation of a monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic (see PCT application WO 93/02197 in the name of Scott et al., which discloses the nucleotide sequence of a callase). DNA molecules which contain chitinase-encoding sequences can be obtained, for example, from the ATCC under Accession Nos. 39637 and 67152 (see also Kramer et al., (1993) *Insect Biochem. Molec. Biol.* 23: 691, which describes the nucleotide sequence of a cDNA encoding tobacco hookworm chitinase, and Kawalleck et al., (1993) *Plant Molec. Biol.* 21: 673, which provides the nucleotide sequence of parsley ubi4-2 polyubiquitin).

(K) A molecule that stimulates signal transduction. For example, see the disclosure by Botella et al., (1994) *Plant Molec. Biol.* 24: 757, of nucleotide sequences for mung bean calmodulin cDNA clones, and Griess et al., (1994) *Plant Physio.* 104: 1467, which provides the nucleotide sequence of a maize calmodulin cDNA clone.

(L) A hydrophobic moment peptide (see PCT application WO 95/16776 which discloses peptide derivatives of Tachyplesin which inhibit fungal plant pathogens, and PCT application WO 95/18855 which teaches synthetic antimicrobial peptides that confer disease resistance).

(M) A membrane permease, a channel former or a channel blocker. For example, see the disclosure by Jaynes et al., (1993) *Plant Sci.* 89: 43), of heterologous expression of a cecropin-β lytic peptide analog to render transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the nucleic acid encoding the coat protein is derived, as well as by related viruses (see Beachy et al., (1990) *Ann. Rev. Phytopathol.* 28: 451). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus (Id.).

(O) An insect-specific antibody or an immunotoxin derived therefrom. Thus, an antibody targeted to a critical metabolic function in the insect gut would inactivate an affected enzyme, killing the insect (Cf. Taylor et al., Abstract #497, SEVENTH INT'L SYMPOSIUM ON MOLECULAR PLANT-MICROBE INTERACTIONS (Edinburgh, Scotland, 1994); enzymatic inactivation in transgenic tobacco via production of single-chain antibody fragments).

(P) A virus-specific antibody (see, for example, Tavia-doraki et al., (1993) *Nature* 366: 469; showing that transgenic plants expressing recombinant antibody are protected from virus attack).

(Q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase (see Lamb et al., (1992) *Bio/Technology* 10: 1436). The cloning and characterization of a nucleic acid which encodes a bean endopolygalacturonase-inhibiting protein is described by Toubart et al., (1992) *Plant J.* 2: 367.

(R) A developmental-arrestive protein produced in nature by a plant. For example, Logemann et al., (1992) *Bio/Technology* 10: 305, have shown that transgenic plants expressing the barley ribosome-inactivating nucleic acid have an increased resistance to fungal disease.

(S) Nucleic acids involved in the Systemic Acquired Resistance (SAR) Response and/or the pathogenesis related nucleic acids. Briggs, S., *Current Biology,* 5(2) (1995), Pieterse & Van Loon (2004) *Curr. Opin. Plant Bio.* 7(4):456 64 and Somssich (2003) *Cell* 113(7):815 6.

(T) Nucleic acids encoding resistance to fungi (Cornelissen and Melchers, *Pl. Physiol.* 101:709 712, (1993) and Parijs et al., *Planta* 183:258 264, (1991) and Bushnell et al., *Can. J. Plant Pathol.* 20(2):137 149 (1998). Also see U.S. application Ser. No. 09/950,933.

2. Transgenes that Confer Resistance to a Herbicide, for Example:

(A) An herbicide that inhibits the growing point or meristem, such as an imidazalinone or a sulfonylurea. Exemplary transgenes or nucleic acids in this category code for mutant ALS or AHAS enzyme as described, for example, by Lee et al., (1988) *EMBO J.* 7: 1241, and Miki et al., (1990) *Theor. Appl. Genet.* 80: 449, respectively.

(B) Glyphosate (resistance imparted by mutant 5-enolpyruvl-3-phosphikimate synthase (EPSP) and aroA nucleic acids) and other phosphono compounds such as glufosinate (phosphinothricin acetyl transferase (PAT) and *Streptomyces hygroscopicus* phosphinothricin acetyl transferase (bar) nucleic acids), and pyridinoxy or phenoxy proprionic acids and cycloshexones (ACCase inhibitor-encoding nucleic acids). See, for example, U.S. Pat. No. 4,940,835 to Shah et al., which discloses the nucleotide sequence of a form of EPSP which can confer glyphosate resistance. A DNA molecule encoding a mutant aroA can be obtained under ATCC accession No. 39256, and the mutant nucleotide sequence is disclosed in U.S. Pat. No. 4,769,061 to Comai. European patent application No. 0 333 033 to Kumada et al. and U.S. Pat. No. 4,975,374 to Goodman et al. discloses nucleotide sequences encoding glutamine synthetase which confers resistance to herbicides such as L-phosphinothricin. The nucleotide sequence encoding a phosphinothricin-acetyl-transferase is provided in European application No. 0 242 246 to Leemans et al. De Greef et al., (1989) *Bio/Technology* 7: 61, describes the production of transgenic plants that express chimeric bar coding for phosphinothricin acetyl transferase activity. Exemplary nucleic acids conferring resistance to phenoxy proprionic acids and cycloshexones, such as sethoxydim and haloxyfop, are the Acct-S1, Acc1-S2 and Acc1-S3 nucleic acids described by Marshall et al., (1992) *Theor. Appl. Genet.* 83: 435.

(C) An herbicide that inhibits photosynthesis, such as a triazine (psbA and gs+) and a benzonitrile (nitrilase). Przibilla et al., (1991) *Plant Cell* 3: 169, describe the transformation of *Chlamydomonas* with plasmids encoding mutant psbA. Nucleic acids encoding nitrilase are disclosed in U.S. Pat. No. 4,810,648 to Stalker, and these nucleic acids are available under ATCC Accession Nos. 53435, 67441 and 67442. Cloning and expression of DNA coding for a glutathione S-transferase is described by Hayes et al., (1992) *Biochem. J.* 285: 173.

3. Transgenes that Confer or Contribute to a Value-Added Trait, such as:

(A) Decreased phytate content: Introduction of a phytase-encoding nucleic acid would enhance breakdown of phytate, adding more free phosphate to the transformed plant. For example, see Van Hartingsveldt et al., (1993) *Gene* 127: 87, for a disclosure of the nucleotide sequence of an *Aspergillus niger* phytase.

(B) Modified carbohydrate composition effected, for example, by transforming plants with a nucleic acid encoding an enzyme that alters the branching pattern of starch (see Shiroza et al., (1998) *J. Bacteriol.* 170: 810, nucleotide sequence of *Streptococcus mutans* fructosyltransferase; Steinmetz et al., (1985) *Mol. Gen. Genet.* 200: 220, nucleotide sequence of *Bacillus subtilis* levansucrase; Pen et al., (1992) *Bio/Technology* 10: 292, production of transgenic plants that express *Bacillus licheniformis* α-amylase; Elliot et al., (1993) *Plant Molec. Biol.* 21: 515, nucleotide sequences of tomato invertase; Søgaard et al., (1993) *J. Biol. Chem.* 268: 22480, site-directed mutagenesis of barley α-amylase nucleic acid; and Fisher et al., (1993) *Plant Physiol.* 102: 1045, maize endosperm starch branching enzyme II).

Those skilled in the art will appreciate that the transgenes described above may also be transferred into tobacco plants using conventional breeding techniques as known in the art and as described herein.

As a further alternative, the transgene can encode an antisense RNA molecule or any other non-translated RNA as known in the art. In a further alternative embodiment, the transgene effects gene suppression in the host plant.

C. Methods for Tobacco Transformation.

Plants can be transformed according to the present invention using any suitable method known in the art. Intact plants, plant tissue, explants, meristematic tissue, protoplasts, callus tissue, cultured cells, and the like may be used for transformation depending on the plant species and the method employed. Procedures for transforming a wide variety of plant species are well known and routine in the art and described throughout the literature. Such methods include, but are not limited to, transformation via bacterial-mediated nucleic acid delivery, viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

Bacterial mediated nucleic acid delivery includes but is not limited to DNA delivery by *Agrobacterium* spp. and is described, for example, in Horsch et al. (*Science* 227:1229 (1985); Ishida et al. (*Nature Biotechnol.* 14:745 750 (1996); and Fraley et al. (*Proc. Natl. Acad. Sci.* 80: 4803 (1983)). Transformation by various other bacterial species is described, for example, in Broothaerts et al. (*Nature* 433:629-633 (2005)).

Physical delivery of nucleotide sequences via microparticle bombardment is also well known and is described, for example, in Sanford et al. (*Methods in Enzymology* 217:483-509 (1993)) and McCabe et al. (*Plant Cell Tiss. Org. Cult.* 33:227-236 (1993)).

Another method for physical delivery of nucleic acid to plants is sonication of target cells. This method is described, for example, in Zhang et al. (*Bio/Technology* 9:996 (1991)). Nanoparticle-mediated transformation is another method for delivery of nucleic acids into plant cells (Radu et al., *J. Am. Chem. Soc.* 126: 13216-13217 (2004); Torney, et al. *Society for In Vitro Biology*, Minneapolis, Minn. (2006)). Alternatively, liposome or spheroplast fusion can be used to introduce nucleotide sequences into plants. Examples of the use of liposome or spheroplast fusion are provided, for example, in Deshayes et al. (*EMBO J.*, 4:2731 (1985), and Christou et al. (*Proc Natl. Acad. Sci. U.S.A.* 84:3962 (1987)). Direct uptake of nucleic acid into protoplasts using $CaCl_2$ precipitation, polyvinyl alcohol or poly-L-ornithine is described, for example, in Hain et al. (*Mol. Gen. Genet.* 199:161 (1985)) and Draper et al. (*Plant Cell Physiol.* 23:451 (1982)). Electroporation of protoplasts and whole cells and tissues is described, for example, in Donn et al. (In *Abstracts of VIIth International Congress on Plant Cell and Tissue Culture IAPTC*, A2-38, p 53 (1990); D'Halluin et al. (*Plant Cell* 4:1495-1505 (1992)); Spencer et al. (*Plant Mol. Biol.* 24:51-61 (1994)) and Fromm et al. (*Proc. Natl. Acad. Sci.* 82: 5824 (1985)). Polyethylene glycol (PEG) precipitation is described, for example, in Paszkowski et al. (*EMBO J.* 3:2717 2722 (1984)). Microinjection of plant cell protoplasts or embryogenic callus is described, for example, in Crossway (*Mol. Gen. Genetics* 202:179-185 (1985)). Silicon carbide whisker methodology is described, for example, in Dunwell et al. (*Methods Mol. Biol.* 111:375-382 (1999)); Frame et al. (*Plant J.* 6:941-948 (1994)); and Kaeppler et al. (*Plant Cell Rep.* 9:415-418 (1990)).

Plant cells, which have been transformed by any method known in the art, can also be regenerated to produce intact plants using known techniques.

Plant regeneration from cultured protoplasts is described in Evans et al., *Handbook of Plant Cell Cultures*, Vol. 1: (MacMilan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues.

Means for regeneration vary from species to species of plants, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. A large number of plants have been shown capable of regeneration from transformed individual cells to obtain transgenic whole plants.

The regenerated plants are transferred to standard soil conditions and cultivated in a conventional manner. The plants are grown and harvested using conventional procedures.

The foregoing methods for transformation may be used for producing transgenic inbred lines. Transgenic inbred lines can then be crossed, with another (non-transformed or transformed) inbred line, in order to produce a transgenic hybrid tobacco plant. Alternatively, a genetic trait that has been engineered into a particular tobacco line using the foregoing transformation techniques can be moved into another line using traditional backcrossing techniques that are well known in the plant breeding arts. For example, a backcrossing approach can be used to move an engineered trait from a non-elite line into an elite tobacco line, or from a hybrid tobacco plant containing a foreign nucleic acid in its genome into a line or lines, which do not contain that nucleic acid. As used above, "crossing" can refer to a simple X by Y cross, or the process of backcrossing, depending on the context.

VI. Products

Tobacco plants, or parts thereof, of the present invention may be utilized in any product containing tobacco including without limitation pipe, cigar and cigarette tobacco, and chewing tobacco, snuff, and tobacco-containing gum and lozenges; and may be in any form including leaf tobacco, shredded tobacco, cut tobacco, or tobacco extract. Accordingly, some embodiments of the invention provide tobacco products produced from the plants of the present invention, or parts thereof. The tobacco plants of the invention, or parts thereof, can be also used in blends with tobacco from other tobacco varieties to make a tobacco product VII. Industrial Applicability This invention is also directed to methods for producing a tobacco plant by crossing a first parent tobacco plant with a second parent tobacco plant wherein either the first or second parent tobacco plant is a tobacco plant of cultivar AOB 175 or a tobacco plant of cultivar AOB 175 further comprising one or more additional traits (e.g., single gene traits). Further, both first and second parent tobacco plants can come from cultivar AOB 175 or a tobacco plant of cultivar AOB 175 further comprising one or more traits (e.g., single gene traits). Thus, any such methods using the tobacco cultivar AOB 175 or a tobacco plant of AOB 175 further comprising one or more additional traits (e.g., one or more single gene traits) are part of this invention: selfing, backcrosses, doubled-haploid production, hybrid production, crosses to populations, and the like. All plants produced using tobacco cultivar AOB 175 or modified cultivar AOB 175 further comprising one or more additional traits (e.g., one or more single gene traits) as a parent are within the scope of this invention. Advantageously, tobacco cultivar AOB 175 or modified cultivar AOB 175 further comprising one or more additional traits (e.g., one or more single gene traits) are used in crosses with other, different, tobacco inbreds to produce first generation ($F_1$) tobacco hybrid seeds and plants with superior characteristics.

VIII. Deposits

A deposit of at least 2500 seeds of tobacco cultivar AOB 175 has been made with the American Type Culture Collection (ATCC), Manassas, VA 20110 USA on Nov. 6, 2008. The deposit has been assigned ATCC Accession Number PTA-9589. This deposit of the tobacco cultivar AOB 175 will be maintained in the ATCC depository, which is a public depository, for a period of 30 years, or 5 years after the most recent request, or for the effective life of the patent, whichever is longer, and will be replaced if it becomes nonviable during that period. Applicants do not waive any infringement of their rights granted under this patent or under the Plant Variety Protection Act (7 U.S.C. 2321 et seq.).

Having now described the invention, the same will be illustrated with reference to certain examples, which are included herein for illustration purposes only, and which are not intended to be limiting of the invention.

That which is claimed is:

1. A method for producing an AOB 175-derived tobacco plant comprising:
   (a) crossing tobacco cultivar AOB 175, representative seed of said tobacco cultivar AOB 175 having been deposited under ATCC Accession No. PTA-9589, with a second tobacco plant to yield progeny tobacco seed;
   (b) growing said progeny tobacco seed, under plant growth conditions, to yield said AOB 175-derived tobacco plant;
   (c) crossing said AOB 175-derived tobacco plant with itself or another tobacco plant to yield additional AOB 175-derived progeny tobacco seed;
   (d) growing said progeny tobacco seed of step (a) under plant growth conditions, to yield additional AOB 175-derived tobacco plants; and
   (e) repeating the crossing and growing steps of (a) and (b) from 0 to 7 times to generate further AOB 175-derived tobacco plants.

2. A method of introducing a desired trait into tobacco cultivar AOB 175, comprising:
   (a) crossing tobacco cultivar AOB 175, representative seed of said tobacco cultivar AOB 175 having been deposited under ATCC Accession No. PTA-9589, with a second tobacco plant that comprises a desired trait to produce F1 progeny;
   (b) selecting an F1 progeny that comprises the desired trait;
   (c) crossing the selected F1 progeny with tobacco cultivar AOB 175, representative seed of said tobacco cultivar AOB 175 having been deposited under ATCC Accession No. PTA-9589, to produce backcross progeny;
   (d) selecting backcross progeny comprising the desired trait and the physiological and morphological characteristics of tobacco cultivar AOB 175; and
   (e) repeating steps (c) and (d) from 0 to 7 times in succession to produce selected backcross progeny that comprise the desired trait and the physiological and morphological characteristics of tobacco cultivar AOB 175 when grown in the same environmental conditions.

3. The method of claim 2, wherein the trait is selected from the group consisting of herbicide tolerance, insect resistance, disease resistance, nematode resistance, tolerance to abiotic stress, yield enhancement, improved leaf characteristics, altered reproductive capability, and altered chemical composition.

4. A tobacco plant produced by the method of claim 2.

5. A tobacco plant produced by the method of claim 3.

* * * * *